(12) United States Patent
Yokoyama et al.

(10) Patent No.: US 8,853,256 B2
(45) Date of Patent: *Oct. 7, 2014

(54) COMPOSITION FOR PREVENTING THE OCCURRENCE OF CARDIOVASCULAR EVENT IN MULTIPLE RISK PATIENT

(75) Inventors: Mitsuhiro Yokoyama, Hyogo (JP); Hideki Origasa, Toyama (JP); Masunori Matsuzaki, Yamaguchi (JP); Yuji Matsuzawa, Hyogo (JP); Yasushi Saito, Chiba (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/302,790

(22) PCT Filed: May 31, 2007

(86) PCT No.: PCT/JP2007/061099
§ 371 (c)(1),
(2), (4) Date: Nov. 26, 2008

(87) PCT Pub. No.: WO2007/142118
PCT Pub. Date: Dec. 13, 2007

(65) Prior Publication Data
US 2009/0156675 A1 Jun. 18, 2009

(30) Foreign Application Priority Data
May 31, 2006 (JP) .................................. 2006-152740

(51) Int. Cl.
*A61K 31/232* (2006.01)
*A61K 31/40* (2006.01)
*A61K 31/366* (2006.01)
*A61K 31/225* (2006.01)
*A61K 31/202* (2006.01)
*A61K 31/22* (2006.01)
*A61K 45/06* (2006.01)
*A61K 31/351* (2006.01)

(52) U.S. Cl.
CPC ............... *A61K 31/22* (2013.01); *A61K 31/232* (2013.01); *A61K 45/06* (2013.01); *A61K 31/351* (2013.01)
USPC ........... 514/423; 514/549; 514/510; 514/460; 514/560

(58) Field of Classification Search
USPC ........................................................ 514/560
See application file for complete search history.

(56) References Cited

U.S. PATENT DOCUMENTS 5,260,305 A * 11/1993 Dennick .................. 514/255.06
5,656,667 A * 8/1997 Breivik et al. ................ 514/560
5,753,703 A * 5/1998 Cavazza et al. .............. 514/556
6,174,865 B1 * 1/2001 Klein ............................. 514/29
2004/0009208 A1 * 1/2004 Edson et al. ................. 424/439
2005/0113449 A1 * 5/2005 Renshaw ...................... 514/560
2007/0021504 A1 1/2007 Yokoyama et al.

FOREIGN PATENT DOCUMENTS

| EP | 1 157 692 A1 | 11/2001 |
| EP | 1790339 A1 | 5/2007 |
| WO | WO00/48592 | * 8/2000 |
| WO | WO-00/48592 A1 | 8/2000 |
| WO | WO-2007/007686 A1 | 1/2007 |

OTHER PUBLICATIONS

Yorioka et al. Lipid-lowering therapy and coagulation/fibroinolysis parameters in patients on peritoneal dialysis. The international journal of artificial organs, Jan. 2000 vol. 23, No. 1, pp. 27-32.*
Medical Drug Interview Form, EPA Preparation, EPADEL Capsules 300, Revised in Jul. 2002 and Feb. 2004, pp. 21-22, 21st Edition, issued in Dec. 2004.
'AHA Hatsu Sokuho Jelis Kekka Happyo', Medical Tribune, (Nov. 17, 2005), Tokubetsu Kikaku Dai 3 Bu, pp. 75 to 76, (cited in the description of the present application as "non-patent document 2") (Doitsu Naiyo no Website Kiji: URL, http://www.medical-tribune.jp/congress/jelis/jelis.html.
Yokoyama, M. et al., American Heart Journal, (2003), vol. 146, No. 4, pp. 613-620.
Yuichi Ishikawa, 'Jelis no Jisshi Keikaku to Kitai sareru Kekka', [online], Jelis Medical Asahi (Medical Asahi 1996,12 Bassui), Mar. 29, 2007 Access], Internet, URL, http://www.mochida.co.jp/dis/jelis/jInwepm2.html.
Yasushi Saito, 'Fukusu no Risk Inshi ga Juseki shita Shorei no Kandomyaku Event Ichiji Yobo no Okeru EPA Seizai no Yuyosei', [online] AHA2006 Sokuho Jelis Sub Kaiseki Kekka Happyo [Mar. 29, 2007, Access], Internet, URL, http://www.jelis.jp/mt/aha2006/01_01.html.http://www.mtrib.com/mt/aha2006/01_01.html.
Mochida Pharmaceutical Co., Ltd. New Release, "'Epadel' ga Kandomyaku Shikkan no Hassho to Saihatsu o Yokusei Daikibo Shiken 'JELIS' no Aratana Kaiseki Kekka ga Kohyo sare mashita", Nov. 15, 2006 Happyo, URL, http://www.mochida.co.jp/news/2006/pdf/1115.pdf.
Yokoyama, M et al., Lancet (2007), vol. 369, No. 9567, pp. 1090-1098, (cited in the description of the present application as "non-patent document 3").
Adan et al., "Effects of docosahexaenoic and eicosapentaenoic acid on lipid metabolism, eicosanoid production, platelet aggregation and atherosclerosis in hypercholesterolemic rats", Bioscience, Biotechnology, and Biochemistry, vol. 63, No. 1, pp. 111-119, (Jan. 1999). XP002613171.
European Search Report dated Dec. 21, 2010, for European Patent Appl. No. 07744487.5.

(Continued)

*Primary Examiner* — Jennifer M Kim
(74) *Attorney, Agent, or Firm* — Birch, Stewart, Kolasch & Birch, LLP

(57) ABSTRACT

Disclosed is a composition which is useful for preventing the occurrence of a cardiovascular event, particularly a composition which is expected to show a prophylactic effect on a cardiovascular event occurring in a hypercholesterolemia patient despite providing the patient with a treatment with HMG-CoA RI or a cardiovascular event occurring in a multiple risk patient.

14 Claims, 1 Drawing Sheet

(56) References Cited

OTHER PUBLICATIONS

Mochida Pharmaceutical Co., Ltd. News Release "Mochida Announces Completion of 'JELIS' Major Clinical Trial for 'EPADEL' Hyperlipidemia and Arteriosclerosis Obliterans Therapeutic Treatment" http://www.mochida.co.jp/english/news/2005/0322.html, Mar. 22, 2005.

Fruchart et al., "The Residual Risk Reduction Intiative: A Call to Action to Reduce Residual Vascular Risk in Patients with Dyslipidemia," Am. J. Cardiol. (2008), vol. 102, [Suppl]: pp. 1K-34K.

Kastelein et al,. Simvastatin with or without Ezetimibe in Familial Hypercholesterolemia, N. Engl. J. Med. (2008), vol. 358, pp. 1431-1443.

Yokoyama et al., "Effects of Eicosapentaenoic Acid (EPA) on Major Cardiovascular Events in Hypercholesterolemic Patients," The Japan EPA Lipid Intervention Study (JELIS), Slides 1-30 (2005).

Yokoyama, M., "Effects of Eicosapentaenoic Acid (EPA) on Major Cardiovascular Events in Hypercholesterolemic Patients: the Japan EPA Lipid Intervention Study (JELIS)," Circulation, Late-Breaking Clinical Trial Abstracts, vol. 112, No. 21, pp. 3362-3364, 2005.

Yokoyama, M., "JELIS Revealed EPA Preparation's Inhibitory Action on Coronary Events," Announcement at AHA 2005, Dallas, Texas, Nov. 14, 2005.

* cited by examiner

COMPOSITION FOR PREVENTING THE OCCURRENCE OF CARDIOVASCULAR EVENT IN MULTIPLE RISK PATIENT

TECHNICAL FIELD

This invention relates to a composition for preventing occurrence of cardiovascular events (primary prevention) in multiple risk patients, the composition containing at least ethyl icosapentate (hereinafter abbreviated as EPA-E).

BACKGROUND ART

Westernization of diet has resulted in the increase of patients suffering from lifestyle-related diseases such as diabetes, hyperlipidemia, and hypertension. Some of these diseases finally lead to arteriosclerotic diseases such as myocardial infarction, angina pectoris, and cerebral infarction. Treatment of the lifestyle-related diseases is based on the improvement of lifestyle, and more specifically, on the alimentary therapy and kinesitherapy. However, such improvement of the dietary life or the lack of exercise is often difficult in the patients suffering from the "lifestyle-related diseases", and they usually transfer to pharmacotherapy in order to prevent poor prognosis, for example, onset of myocardial infarction or cerebral infarction.

An exemplary compound having the action of improving such lifestyle-related diseases is polyunsaturated fatty acid. The polyunsaturated fatty acid is defined as a fatty acid including two or more carbon-carbon double bonds in one molecule, and the polyunsaturated fatty acids are categorized by the position of the double bond into $\omega$3 fatty acid, $\omega$6 fatty acid, and the like. The $\omega$3 polyunsaturated fatty acids include $\alpha$-linolenic acid, icosapentaenoic acid (EPA), and docosahexaenoic acid (DHA), and the $\omega$6 polyunsaturated fatty acids include linoleic acid, $\gamma$-linolenic acid, and arachidonic acid. Polyunsaturated fatty acids are derived from natural products, and exhibit various actions including antiarteriosclerotic action, platelet aggregation inhibitory action, hypolipidemic action, antiinflammatory action, antitumor action, and central action, and due to the high safety, polyunsaturated fatty acids are incorporated in various kinds of food, or sold as a health food or drug.

Decrease in the death rate in the patients who have history of suffering from myocardial infarction has been reported for the administration of a mixture of ethyl ester of an $\omega$-3 polyunsaturated fatty acid EPA (EPA-E) and ethyl ester of an $\omega$-3 polyunsaturated fatty acid DHA (DHA-E) for 3.5 years (see Patent Document 1). However, the results disclosed in Patent Document 1 relates to the secondary prevention, that is, prevention of recurrence, and the drug which is effective in the secondary prevention is not always effective in the primary prevention.

Based on the results of animal experiments and small scale clinical observations, many large scale clinical trials have been recently planned and conducted for the purpose of confirming whether various drugs which are effective in improving the lifestyle-related diseases can also prevent arteriosclerotic diseases in human. The results, however, have not necessarily been as intended, and the situation is still severe for the prevention of the occurrence of cardiovascular events in the case of patients suffering from a plurality of risk factors.

High purity EPA-E is commercially available in the trade names of Epadel™ and Epadel S™ (manufactured by Mochida Pharmaceutical Co., Ltd.) as therapeutic drugs for hyperlipidemia. There has been reported that when such high purity EPA-E is orally administered at 600 mg per administration and 3 times a day immediately after meal (when TG is abnormal, the dose is increased to the level of 900 mg per administration and 3 times a day), serum T-Cho concentration can be reduced by 3 to 6%, and serum TG can be reduced by 14 to 20% (see Non-Patent Document 1). There has also been reported in The Heart Failure Society of America 2005 Annual Meeting that, based on such action, such high purity EPA-E was expected to have the effects of improving cardiovascular events in hyperlipidemia patients, and combined use with HMG-CoA RI was effective in inhibiting cardiac events in a large scale clinical trial. In this large scale clinical trial (JELIS, Japan EPA Lipid Intervention Study)), statistically significant suppression of the cardiac events by the EPA-E was confirmed for the total of the primary prevention patients and secondary prevention patients, and for the secondary prevention patients. On the other hand, in the analysis limited to the primary prevention patients, the incidence of the events was lower in the EPA-E group (the group administered with EPA-E in combination with HMG-CoA RI) compared to the control group (the group administered with solely with HMG-CoA RI), while this difference was not statistically significant. This trial also revealed that after 5 years from the start of the trial, the LDL-cholesterol value reduced by 26% in both of the EPA-F group and control group, that no significant difference was found between these groups, and that change of the HDL-cholesterol value was slight in both groups (see Non-Patent Document 2). This trial also revealed that the total cholesterol and the LDL-cholesterol decreased by 19% and 25%, respectively, in both of the EPA-E group and the control group, and that triglyceride decreased by 9% (significant) and 4% in the EPA-E group and the control group, respectively, while little change in HDL-C was noted in both of the EPA-E group and the control group (see Non-Patent Document 3). There is so far no report that has analyzed prevention of the occurrence of the cardiovascular events in the case of patients having two or more risk factors.

Patent Document 1: WO 00/48592 (JP 2002-537252 A)
Non-Patent Document 1: Drug Interview Form "EPA preparation, Epadel capsule 300", revised in July, 2002 and February, 2004, version 21 issued in December, 2004; pp. 21-22.
Non-Patent Document 2: Medical Tribune, issue of Nov. 17, 2005, Feature article 3, pp. 75-76.
Non-Patent Document 3: Lancet, vol. 369, pages 1090 to 1098 (2007).

DISCLOSURE OF THE INVENTION

Problems to be Solved by the Invention

In view of the situation that there is a serious problem that death from the cardiovascular disease is still a major cause of the death, and many cases of cardiovascular events are still impossible to prevent by the HMG-CoA RI therapy, an object of the present invention is to provide a composition for preventing onset of the cardiovascular events.

Means to Solve the Problems

In order to solve the problems as described above, the inventors of the present invention made an extensive study on a therapy of hypercholesterolemia patients and found that EPA-E has the effect of preventing occurrence of the cardiovascular events in patients suffering from multiple risk factors, and in particular, the effect of preventing occurrence of the cardiovascular events in male patients suffering from multiple risk factors. The present invention has been completed on the bases of such finding. Accordingly, the present invention is directed to the following:

(1) A composition for preventing occurrence of a cardiovascular event (primary prevention) in a hypercholesterolemia patient, the composition containing at least EPA-E as its effective component, wherein the patient also suffers from at least one risk factor selected from the group consisting of
 (1) obesity,
 (2) hypertension or prehypertension,
 (3) diabetes, prediabetes, or abnormal glucose tolerance, and
 (4) hypertriglyceridemia and/or low HDL cholesterolemia.

(2) A composition for preventing occurrence of a cardiovascular event in a hypercholesterolemia patient, the composition containing at least EPA-E as its effective component, wherein the hypercholesterolemia patient is a patient also suffering from two or more of the risk factors.

(3) A composition for preventing occurrence of a cardiovascular event in a hypercholesterolemia patient, the composition containing at least EPA-E as its effective component, wherein the patient also suffers from at least one of risk factors as defined by a body mass index (BMI) of at least 25 for the obesity; by a systolic blood pressure (SBP) of at least 140 mmHg or a diastolic blood pressure (DBP) of at least 90 mmHg for the hypertension or the prehypertension; by a fasting blood glucose (FBS) of at least 126 mg/dL or a hemoglobin A1c (HbA1c) of at least 6.5% for the diabetes, the prediabetes, or the abnormal glucose tolerance; and by triglyceride (TG) of at least 150 mg/dL and/or a HDL-C of less than 40 mg/dL for the hypertriglyceridemia and/or the low HDL cholesterolemia.

(4) The composition according to any one of (1) to (3) above, wherein the content of the EPA-E is at least 96.5% by weight in relation to the total content of fatty acid and derivatives thereof.

(5) The composition according to any one of (1) to (4) above, wherein the EPA-E is orally administered at a dose of 1.8 g/day to 2.7 g/day.

(6) The composition according to any one of (1) to (5) above, wherein the composition is used in combination with HMG-CoA RI.

(7) The composition according to any one of (1) to (6) above, wherein the hypercholesterolemia patient is a male patient.

(8) The composition according to any one of (1) to (7) above, wherein the hypercholesterolemia patient is a patient also suffering from hypertriglyceridemia and low HDL cholesterolemia.

(9) A method for preventing occurrence of a cardiovascular event in a hypercholesterolemia patient by administering the patient with the composition according to any one of (1) to (8) above.

(10) Use of the composition according to any one of (1) to (8) above for the manufacture of an agent for preventing occurrence of a cardiovascular event in a hypercholesterolemia patient.

Merits of the Invention

The above-mentioned composition of the present invention containing at least EPA-E as its effective component is effective in preventing occurrence of cardiovascular events in hypercholesterolemia patients, and in particular, in preventing occurrence of cardiovascular events in hypercholesterolemia patients who have been treated with HMG-CoA RI but still suffer from the risk of the cardiovascular events, or more particularly, in preventing occurrence of cardiovascular events in hypercholesterolemia patients also suffering from at least one risk factor selected from the group consisting of
 (1) obesity,
 (2) hypertension or prehypertension,
 (3) diabetes, prediabetes, or abnormal glucose tolerance, and
 (4) hypertriglyceridemia and/or low HDL cholesterolemia.

The effect of the composition of the present invention will be synergistically improved by combined use with the HMG-CoA RI, and such use of the composition of the present invention with the HMG-CoA RI has clinical utility since the effect of preventing the cardiovascular event occurrence is expected to be improved.

BEST MODE FOR CARRYING OUT THE INVENTION

Figure 1:
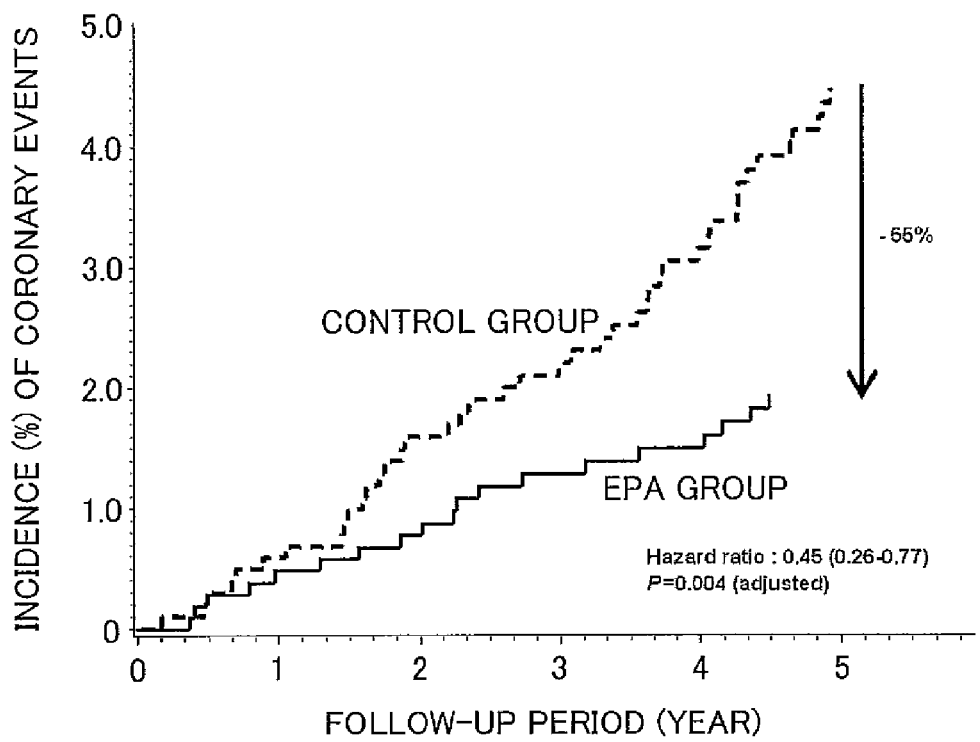
FIG. 1 is a graph prepared by plotting the incidence of the cardiovascular events in Y-axis and the time after the start of the trial in X-axis for male patients having at least 2 risk factors.

Next, the present invention is described in detail.

A first aspect of the present invention provides a composition for preventing occurrence of a cardiovascular event (primary prevention) in a hypercholesterolemia patient, the composition containing at least EPA-E as its effective component, wherein the patient also suffers from at least one risk factor selected from the group consisting of
 (1) obesity,
 (2) hypertension or prehypertension,
 (3) diabetes, prediabetes, or abnormal glucose tolerance, and
 (4) hypertriglyceridemia and/or low HDL cholesterolemia.

Alternatively, the first aspect of the present invention provides a composition for preventing occurrence of a cardiovascular event (primary prevention) in a hypercholesterolemia patient, the composition containing at least EPA-E and/or DHA-E as its effective component, wherein the patient also suffers from at least one risk factor selected from the group consisting of
 (1) obesity,
 (2) hypertension or prehypertension,
 (3) diabetes, prediabetes, or abnormal glucose tolerance, and
 (4) hypertriglyceridemia and/or low HDL cholesterolemia.

The prevention of the occurrence of the cardiovascular events include all cases of primary prevention, and exemplary cases include prevention of cardiovascular death, fatal myocardial infarction, sudden cardiac death, nonfatal myocardial infarction, cardiovascular angioplasty, new occurrence of rest angina and exercise-induced angina, and destabilization of the angina. The composition of the present invention may be administered to any person who needs prevention of the occurrence of the cardiovascular events, and typical such patients are hypercholesterolemia patients.

A second aspect of the present invention provides a composition for preventing occurrence of a cardiovascular event in a hypercholesterolemia patient undergoing a HMG-CoA RI therapy, the composition containing at least EPA-E, wherein the patient also suffers from at least one risk factor selected from the group consisting of (1) obesity,
(2) hypertension or prehypertension,
(3) diabetes, prediabetes, or abnormal glucose tolerance, and
(4) hypertriglyceridemia and/or low HDL cholesterolemia.

Alternatively, the second aspect of the present invention provides a composition for preventing occurrence of a cardiovascular event in a hypercholesterolemia patient undergoing a HMG-CoA RI therapy, the composition containing at least EPA-E and/or DHA-E, wherein the patient also suffers from at least one risk factor selected from the group consisting of (1) obesity,
(2) hypertension or prehypertension,
(3) diabetes, prediabetes, or abnormal glucose tolerance, and
(4) hypertriglyceridemia and/or low HDL cholesterolemia.

While HMG-CoA RI includes all those having inhibitory action for 3-hydroxy-3-methylglutaryl coenzyme A reductase, the one used in the present invention is preferably a pharmaceutically administrable inhibitor which is preferably at least one member selected from the group consisting of pravastatin, simvastatin, lovastatin, fluvastatin, cerivastatin, atorvastatin, pitavastatin, rosuvastatin, and salts and derivatives thereof, and more preferably, pravastatin, lovastatin, simvastatin, fluvastatin, atorvastatin, pitavastatin, or rosuvastatin, and most preferably, pravastatin or simvastatin. All salts are included as long as they are pharmaceutically administrable, and preferred are sodium and calcium salts such as pravastatin sodium, fluvastatin sodium, cerivastatin sodium, atorvastatin calcium, pitavastatin calcium, and rosuvastatin calcium. In the present invention, "pravastatin", for example, also includes the pravastatin in the form of a salt unless otherwise noted.

A third aspect of the present invention provides a composition for preventing occurrence of a cardiovascular event in a hypercholesterolemia patient, the composition containing at least EPA-E as its effective component, wherein the patient also suffers from at least two risk factors selected from the group consisting of (1) obesity,
(2) hypertension or prehypertension,
(3) diabetes, prediabetes, or abnormal glucose tolerance, and
(4) hypertriglyceridemia and/or low HDL cholesterolemia; namely; obesity, and hypertension or prehypertension; obesity, and diabetes, prediabetes, or abnormal glucose tolerance; obesity, and hypertriglyceridemia and/or low HDL cholesterolemia; hypertension or prehypertension, and diabetes, prediabetes or abnormal glucose tolerance; hypertension or prehypertension, and hypertriglyceridemia and/or low HDL cholesterolemia; diabetes, prediabetes, or abnormal glucose tolerance, and hypertriglyceridemia and/or low HDL cholesterolemia; obesity, and hypertension or prehypertension, and diabetes, prediabetes, or abnormal glucose tolerance; obesity, and hypertension or prehypertension, and hypertriglyceridemia and/or low HDL cholesterolemia; obesity, and diabetes, prediabetes, or abnormal glucose tolerance, and hypertriglyceridemia and/or low HDL cholesterolemia; hypertension or prehypertension, and diabetes, prediabetes, or abnormal glucose tolerance, and hypertriglyceridemia and/or low HDL cholesterolemia; obesity, and hypertension or prehypertension, and diabetes, prediabetes, or abnormal glucose tolerance, and hypertriglyceridemia and/or low HDL cholesterolemia. Alternatively, the third aspect of the present invention provides a composition for preventing occurrence of a cardiovascular event in a hypercholesterolemia patient, the composition containing at least EPA-E and/or DHA-E as its effective component, wherein the patient also suffers from at least two risk factors selected from the group consisting of (1) obesity,
(2) hypertension or prehypertension,
(3) diabetes, prediabetes, or abnormal glucose tolerance, and
(4) hypertriglyceridemia and/or low HDL cholesterolemia.

A fourth aspect of the present invention provides a composition for preventing occurrence of a cardiovascular event in a hypercholesterolemia patient, the composition containing at least EPA-E as its effective component, wherein the patient also suffers from at least one, and more preferably, at least two risk factors selected from the group consisting of (1) obesity,
(2) hypertension or prehypertension,
(3) diabetes, prediabetes, or abnormal glucose tolerance, and
(4) hypertriglyceridemia and/or low HDL cholesterolemia.

In this case, the hypercholesterolemia patient is preferably a male patient. Alternatively, the fourth aspect of the present invention provides a composition for preventing occurrence of a cardiovascular event in a hypercholesterolemia patient, the composition containing at least EPA-E and/or DHA-E as its effective component, wherein the patient also suffers from at least one, and more preferably, at least two risk factors selected from the group consisting of (1) obesity,
(2) hypertension or prehypertension,
(3) diabetes, prediabetes, or abnormal glucose tolerance, and
(4) hypertriglyceridemia and/or low HDL cholesterolemia.

In this case, the hypercholesterolemia patient is preferably a male patient.

A fifth aspect of the present invention provides a composition for preventing occurrence of a cardiovascular event in a hypercholesterolemia patient, the composition containing at least EPA-E as its effective component, wherein the patient also suffers from risk factors of hypertriglyceridemia and low HDL cholesterolemia, and more specifically, hypertriglyceridemia and low HDL cholesterolemia with a serum triglyceride (TG) concentration of at least 150 mg/dl and a serum HDL-C concentration of less than 40 mg/dl, or serum TG/HDL-C ratio of at least 3.75. In this case, the hypercholesterolemia patient is preferably a male patient. Alternatively, the fifth aspect of the present invention provides a composition for preventing occurrence of a cardiovascular event in a hypercholesterolemia patient, the composition containing at least EPA-E and/or DHA-E as its effective component, wherein the patient also suffers from risk factors of hypertriglyceridemia and low HDL cholesterolemia, and more specifically, hypertriglyceridemia and low HDL cholesterolemia with a serum triglyceride (TG) concentration of at least 150 mg/dl and a serum HDL-C concentration of less than 40 mg/dl, or a serum TG/HDL-C ratio of at least 3.75. In this case, the hypercholesterolemia patient is preferably a male patient.

A sixth aspect of the present invention provides a composition containing at least EPA-E as its effective component, the composition exhibiting an excellent effect of preventing occurrence of a cardiovascular event in a patient suffering from multiple risk factors who has been administered with this composition for at least 2 years since the start of the administration. Alternatively, the sixth aspect of the present invention provides a composition containing at least EPA-E and/or DHA-E as its effective component, the composition exhibiting an excellent effect of preventing recurrence of a cardiovascular event in a patient suffering from multiple risk factors who has been administered with this composition for at least 2 years since the start of the administration. The hypercholesterolemia patient is preferably a male patient.

A seventh aspect of the present invention provides a method for preventing occurrence of a cardiovascular event in a patient suffering from multiple risk factors by continuously administering the patient with a composition containing at least EPA-E as its effective component for at least 2 years. Alternatively, the seventh aspect of the present invention provides a method for preventing occurrence of a cardiovascular event in a patient suffering from multiple risk factors by continuously administering the patient with a composition containing at least EPA-E and/or DHA-E as its effective component for at least 2 years. The hypercholesterolemia patient is preferably a male patient.

An eighth aspect of the present invention provides a composition for preventing occurrence of a cardiovascular event (primary prevention) in a dyslipidemia patient, the composition containing at least EPA-E as its effective component, wherein the patient also suffers from at least one risk factor selected from the group consisting of
  (1) obesity,
  (2) hypertension or prehypertension,
  (3) diabetes, prediabetes, or abnormal glucose tolerance, and
  (4) hypertriglyceridemia and/or low HDL cholesterolemia.
Alternatively, the eighth aspect of the present invention provides a composition for preventing occurrence of a cardiovascular event (primary prevention) in a dyslipidemia patient, the composition containing at least EPA-E and/or DHA-E as its effective component, wherein the patient also suffers from at least one risk factor selected from the group consisting of
  (1) obesity,
  (2) hypertension or prehypertension,
  (3) diabetes, prediabetes, or abnormal glucose tolerance, and
  (4) hypertriglyceridemia and/or low HDL cholesterolemia.

A ninth aspect of the present invention provides a composition for preventing occurrence of a cardiovascular event (primary prevention) in a hypercholesterolemia patient to be able to administered with HMG-CoA RI, the composition containing at least EPA-E as its effective component, wherein the patient also suffers from at least one risk factor selected from the group consisting of
  (1) obesity,
  (2) hypertension or prehypertension,
  (3) diabetes, prediabetes, or abnormal glucose tolerance, and
  (4) hypertriglyceridemia and/or low HDL cholesterolemia.
Alternatively, the ninth aspect of the present invention provides a composition for preventing occurrence of a cardiovascular event (primary prevention) in a hypercholesterolemia patient to be able to administered with HMG-CoA RI, the composition containing at least EPA-E and/or DHA-E as its effective component, wherein the patient also suffers from at least one risk factor selected from the group consisting of
  (1) obesity,
  (2) hypertension or prehypertension,
  (3) diabetes, prediabetes, or abnormal glucose tolerance, and
  (4) hypertriglyceridemia and/or low HDL cholesterolemia.

While the EPA-E content in the total fatty acid and dosage are not particularly limited as long as intended effects of the present invention are attained, the EPA-E used is preferably the one having a high purity, for example, the one having the proportion of the EPA-E in the total fatty acid and derivatives thereof of preferably 40% by weight or higher, more preferably 90% by weight or higher, and still more preferably 96.5% by weight or higher. The daily dose in terms of EPA-E is typically 0.3 to 6 g/day, preferably 0.9 to 3.6 g/day, and still more preferably 1.8 to 2.7 g/day. Another preferable daily dose is 0.3 to 2.7 g/day, and 0.3 to 1.8 g/day. Another preferable fatty acid included is DHA-E. While the compositional ratio of EPA-E/DHA-E, content of EPA-E and DHA-E (hereinafter referred to as (EPA-E+DHA-E)) in the total fatty acid, and dosage of (EPA-E+DHA-E) are not particularly limited as long as intended effects of the present invention are attained, the composition is preferably the one having a high purity of EPA-E and DHA-E, for example, the one having a proportion of the (EPA-E+DHA-E) in the total fatty acid and derivatives thereof of preferably 40% by weight or higher, more preferably 80% by weight or higher, and still more preferably 90% by weight or higher. The daily dose in terms of EPA-E+DHA-F is typically 0.3 to 10 g/day, preferably 0.5 to 6 g/day, and still more preferably 1 to 4 g/day. Another preferable daily dose is 0.3 to 6 g/day, 0.3 to 4 g/day, and 0.3 to 1 g/day. The content of other long chain saturated fatty acids is preferably low, and among the long chain unsaturated fatty acids, the content of ω6 fatty acids, and in particular, the content of arachidonic acid is preferably as low as less than 2% by weight, and more preferably less than 1% by weight.

The composition of the present invention contains EPA-E and/or DHA-E, and has the effect of preventing occurrence of cardiovascular events in healthy people or those suffering from the risk factors of hyperlipidemia, diabetes, and hypertension when the composition is orally administered, and in particular, of preventing occurrence of cardiovascular events in hypercholesterolemia patients who have been treated with HMG-CoA RI but still suffering from the risk of the cardiovascular events. The composition of the present invention may also be used in combination with the HMG-CoA RI, and such combination may further prevent the occurrence of the cardiovascular events.

The composition of the present invention may be used with other drugs, for example, antiplatelet drugs such as aspirin, ticlopidine, clopidogrel, prasugrel, and cilostazol; anticoagulants such as warfarin, heparin, and ximelagatran; antihypertensive drugs such as angiotensin II receptor antagonists (candesartan, losartan, valsartan, etc.), angiotensin converting enzyme inhibitors, calcium channel antagonists (amlodipine, cilnidipine, etc.), and al blockers; diabetes drugs or abnormal glucose tolerance stimulants such as α-glucosidase inhibitors (voglibose, acarbose, etc.), biguanide drugs, thiazolidinedione drugs (pioglitazone, rosiglitazone, rivoglitazone, etc.), and prompt insulin release promoters (mitiglinide, nateglinide, etc.); antilipotropic drugs and antiarteriosclerotic drugs such as HMG-CoA RI as described above, fibrate drugs, squalene synthetase inhibitors (TAK-475, etc.), and cholesterol absorption inhibitors (ezetimibe, etc.), probucol, anion exchange resin, nicotinic acid drugs, phytostero, elastase, dextran sulfate sodium sulfur, pantothenic acid, and polyene-phosphatidylcholine.

The composition of the present invention contains smaller amounts of impurities such as saturated fatty acids and arachidonic acid which are unfavorable for cardiovascular events compared to fish oil or fish oil concentrate, and accordingly, the intended effects can be attained without causing problems like overnutrition or excessive intake of vitamin A. In addition, since the effective component of the present composition is in the form of an ester, the effective component is more stable to oxidation compared to the case of fish oil in which the effective component is in the form of a triglyceride, and a sufficiently stable composition can be produced by adding a conventional antioxidant. In other words, it is the use of the EPA-E that has for the first time enabled production of a composition for preventing onset of cardiovascular events which can be used in clinical practice.

In the present invention, the term "icosapentaenoic acid" designates all-cis-5,8,11,14,17-icosapentaenoic acid.

In the present invention, the term "hypercholesterolemia patient" means the patient with increased serum T-Cho concentration or serum LDL-Cho concentration. In a narrower sense, this term means the patient suffering from hypercholesterolemia (serum T-Cho concentration of at least about 220 mg/dl, and in more strict sense, at least 250 mg/dl) or high LDL cholesterolemia (serum LDL-Cho concentration of at least 140 mg/dL).

In the present invention, the term "dyslipidemia" is the condition which satisfies at least one of high LDL cholesterolemia (i.e. fasting serum LDL cholesterol value of at least 140 mg/dL), low HDL cholesterolemia (i.e. fasting serum HDL cholesterol value of less than 40 mg/dL), and hypertriglyceridemia (i.e. fasting serum triglyceride value of at least 150 mg/dL) according to the diagnostic criteria described in "Guideline for Preventing Arteriosclerotic diseases, 2007" (edited and published by Japan Atherosclerosis Society).

Of the risk factors treated in the present invention, "obesity" is the state with excessive accumulation of fats in the body. For example, non-limiting examples of the obesity include a body mass index (BMI) of at least 25, a waist measurement of at least 85 cm in male and at least 90 cm in female. "Hypertension" is the state with an abnormal increase in resting arterial blood pressure of the greater circulatory system. For example, in the criteria proposed by Japanese Society of Hypertension at the time of the filing of this application, hypertension is defined as a systolic blood pressure (SBP) of at least 140 mmHg or a diastolic blood pressure (DBP) of at least 90 mmHg. "Prehypertension" is the condition with the blood pressure between the normal blood pressure (or optimal blood pressure) and the blood pressure in the hypertension, and this condition is also referred to as "mild elevated blood pressure" or "borderline hypertension". Non-limiting exemplary criteria for such condition include a systolic blood pressure (SBP) of 120 to 139 mmHg or a diastolic blood pressure (DBP) of 80 to 89 mmHg. In the present invention, "hypertension or prehypertension" means a condition with a systolic blood pressure (SBP) of at least 120 mmHg or a diastolic blood pressure (DBP) of at least 80 mmHg, more strictly, a systolic blood pressure (SBP) of at least 135 mmHg or a diastolic blood pressure (DBP) of at least 85 mmHg, even more strictly a systolic blood pressure (SBP) of at least 140 mmHg or a diastolic blood pressure (DBP) of at least 90 mmHg. "Diabetes" is the glucose metabolism disorder caused by hyposecretion of insulin from the insulin-producing cell ($\beta$ cell) in the pancreas or insufficient action of the insulin in the target cell. Exemplary non-limiting criteria proposed by Japan Diabetes Society at the time of the filing of this application is one of 1) fasting blood glucose of at least 126 mg/dL, 2) 75 g glucose tolerance test at 2 hours of at least 200 mg/dL, and 3) casual blood glucose level of at least 200 mg/dL; or a hemoglobin A1c (HbA1c) of at least 6.5%. The criteria, however, are not limited to these. "Prediabetes" is the condition in which the blood glucose level is between the normal value and the value in the diabetes. "Abnormal glucose tolerance" is the condition in which the blood glucose level in the glucose tolerance test is between the normal value and the value in the diabetes. These conditions are also referred to as the borderline diabetes, prediabetic state, and the diabetic high-risk group. For these conditions, exemplary non-limiting criteria include a fasting blood glucose of 110 to 125 mg/dL, a 75 g glucose tolerance test at 2 hours of 140 to 199 mg/dL, and a hemoglobin A1c (HbA1c) of 5.6 to 6.4%. In the present invention, "diabetes, prediabetes, or abnormal glucose tolerance" means a condition with a fasting blood glucose (FBS) of at least 110 mg/dL or a hemoglobin A1c (HbA1c) of at least 5.6%, more strictly, a fasting blood glucose (FBS) of at least 110 mg/dL or a hemoglobin A1c (HbA1c) of at least 5.9%, and even more strictly with a fasting blood glucose (FBS) of at least 126 mg/dL or a hemoglobin A1c (HbA1c) of at least 6.5%. "Hypertriglyceridemia" is the condition with an increased serum triglyceride (TG) concentration, and strictly, with the serum TG concentration of at least 150 mg/dL. "Low HDL cholesterolemia" is the condition with a reduced serum HDL-C concentration, and strictly, with the serum HDL-C concentration of less than 40 mg/dL. In the present invention, "hypertriqlyceridemia and/or low HDL cholesterolemia" means the state with a serum TG concentration of at least 150 mg/dL and/or a serum HDL-C concentration of less than 40 mg/dL. The hypertriglyceridemia and the low HDL cholesterolemia are both diseases included in the category of dyslipidemia, and they are mutually independent risk factors. Combination of these risk factors, however, is known to result in an increased risk of the occurrence of an arteriosclerotic disease. In the present invention, "the hypertriglyceridemia and/or the low HDL cholesterolemia" is treated as a single risk factor.

In the present invention, the term "combined use of EPA-E with HMG-CoA RI" include both the embodiment in which the EPA-E and the HMG-CoA RI are simultaneously administered and the embodiment in which both agents are separately administered. When these agents are simultaneously administered, they may be formulated either as a single combined drug or separate drugs. When these agents are separately administered, EPA-E may be administered either before or after the HMG-CoA RI. The doses and ratio of the EPA-E and the HMG-CoA RI may be adequately selected.

In the present invention, the term "combined use of EPA-E and/or DHA-E with HMG-CoA RI" include both the embodiment in which the EPA-E and/or DHA-E and the HMG-CoA RI are simultaneously administered and the embodiment in which these agents are separately administered. When these agents are simultaneously administered, they may be formulated either as a single combined drug or separate drugs. When these agents are separately administered, EPA-E and/or DHA-E may be administered either before or after the HMG-CoA RI. The doses and ratio of the EPA-E and/or DHA-E and the HMG-CoA RI may be adequately selected.

The composition of the present invention has the action of preventing onset of the cardiovascular events by the sole administration of the composition, and in particular, the present composition is expected to have the effect of preventing onset of the cardiovascular events which could not be prevented by the sole administration of the HMG-CoA RI. In addition, EPA-E has not only the action of reducing the serum T-Cho concentration and the serum TG, but also the action of suppressing platelet aggregation based on inhibition of arachidonic acid cascade, which is a pharmacological action different from the HMG-CoA RI. Therefore, the action as described above can also be exerted by combined administration with the HMG-CoA RI.

Since EPA-E and DHA-F are highly unsaturated, inclusion of an effective amount of an antioxidant such as butylated hydroxytoluene, butylated hydroxyanisole, propyl gallate, gallic acid, and pharmaceutically acceptable quinone, or $\alpha$-tocopherol is preferable.

The preparation may be orally administered to the patient in the dosage form of tablet, capsule, microcapsule, granules, fine granules, powder, oral liquid preparation, syrup, or jelly. Preferably, the preparation is orally administered by filling in a capsule such as soft capsule or microcapsule.

The soft capsules containing high purity EPA-E (Epadel™ and Epadel S™) are commercially available in Japan as safe therapeutic agents for arteriosclerosis obliterans and hyperlipidemia with reduced side effects, and in such products, proportion of EPA-E in total fatty acid is at least 96.5% by weight. The soft capsule (Omacor™, Ross products, Reliant, and Pronova) containing about 46% by weight of EPA-E and about 38% by weight of DHA-E is commercially available in the U.S., Europe, and other countries as a drug applied for hypertriglyceridemia. These drugs may be purchased for use in the present invention.

The dose and administration period of the composition of the present invention for preventing the onset of the cardiovascular events is the dose and period sufficient for the expression of the intended action, and the dose and administration period may be adequately adjusted depending on the dosage form, administration route, daily frequency, severity of the symptoms, body weight, age, and the like. When orally administered, the composition may be administered at a dose in terms of EPA-E of 0.3 to 6 g/day, preferably 0.9 to 3.6 g/day, and more preferably 1.8 to 2.7 g/day, and while such dose is typically administered in 3 divided doses, if desired, such dose may be administered in a single dose or in several divided doses. The composition is preferably administered during or after the meal, and more preferably, immediately (within 30 minutes) after the meal. When such dose is orally administered, the administration period is typically at least 1 year, preferably at least 2 years, more preferably at least 3 years and still more preferably at least 5 years. The administration, however, is preferably continued as long as there is a considerable risk of onset of the cardiovascular events. If necessary, drug holidays of about 1 day to 3 months, and preferably about 1 week to 1 month may be given.

The HMG-CoA RI is preferably used according to the dosage regimen recommended for the particular drug used, and the dose may be adequately adjusted depending on the type, dosage form, administration route, daily frequency, severity of the symptoms, body weight, gender, age, and the like. When orally administered, the HMG-CoA RI is typically administered at a dose of 0.05 to 200 mg/day, and preferably 0.1 to 100 mg/day in a single dose or in two divided doses. If necessary, the total dose may be administered in several divided doses. The dose of the HMG-CoA RI may be reduced depending on the dose of the EPA-E.

It is to be noted that pravastatin sodium (Mevalotin™ tablets and fine granules, Daiichi Sankyo Co., Ltd.), simvastatin (Lipovas™ tablets, Banyu Pharmaceutical Co., Ltd.), fluvastatin sodium (Lochol™ Tablets, Novartis Pharma K.K. and Tanabe Seiyaku Co., Ltd.), atorvastatin calcium hydrate (Lipitor™ tablets, Astellas Pharma Inc. and Pfizer Inc.), pitavastatin calcium (Livalo™, Kowa Company, Ltd. and Daiichi Sankyo Co., Ltd.), and rosuvastatin calcium (Crestor™ tablets, AstraZeneca and Shionogi & Co., Ltd.) are commercially available in Japan as drugs for treating hyperlipidemia, and lovastatin (Mevacor™ tablets, Merck) is commercially available in the U.S. as a drug for treating hyperlipidemia. These drugs may be purchased and used according to the prescribed dosing schedules.

In the case of pravastatin sodium, the preferable daily dose is 5 to 60 mg, and more preferably 10 to 20 mg, and in the case of simvastatin, the preferable daily dose is 2.5 to 60 mg, and more preferably 5 to 20 mg. In the case of fluvastatin sodium, the preferable daily dose is 10 to 180 mg, and more preferably 20 to 60 mg, and in the case of atorvastatin calcium hydrate, the preferable daily dose is 5 to 120 mg, and more preferably 10 to 40 mg. In the case of pitavastatin calcium, the preferable daily dose is 0.5 to 12 mg, and more preferably 1 to 4 mg, and in the case of rosuvastatin calcium, the preferable daily dose is 1.25 to 60 mg, and more preferably 2.5 to 20 mg. In the case of lovastatin, the preferable daily dose is 5 to 160 mg, and more preferably 10 to 80 mg, and in the case of cerivastatin sodium, the preferable daily dose is 0.075 to 0.9 mg, and more preferably 0.15 to 0.3 mg. The dose, however, is not limited to those as described above.

EXAMPLES

Next, the effects of the composition of the present invention are demonstrated by referring to Examples, which by no means limit the scope of the present invention.

Example 1

Effect of the EPA-F in Preventing Occurrence of Cardiovascular Events in Patients Having Multiple Risk Factors Trial Procedure This trial corresponds to a partial analysis of the results obtained in JELIS (Japan EPA Lipid Intervention Study) which is a large scale clinical trial of high purity EPA preparation which was presented in The Heart Failure Society of America 2005 Annual Meeting (for general information on JELIS, see Medical Tribune, issue of Nov. 17, 2005, Feature article 3, pp. 75-76).

More specifically, for the EPA-E group (7503 cases) and the control group (7478 cases) evaluated for the primary prevention effect in the 18,645 subject patients of the JELIS trial (EPA-E group (9,326 cases) and control group (9,319 cases)), occurrence of the cardiovascular events was observed and analysed for 5 years from the start of the administration in relation to the number of risk factors at the registration as defined by the following (1) to (4):

(1) obesity: body mass index (BMI) of at least 25;

(2) hypertension or prehypertension: systolic blood pressure (SBP) of at least 140 mmHg or diastolic blood pressure (DBP) of at least 90 mmHg;

(3) diabetes, prediabetes, or abnormal glucose tolerance: fasting blood glucose (FBS) of at least 126 mg/dL or hemoglobin A1c (HbA1c) of at least 6.5%;

(4) hypertriglyceridemia or low HDL cholesterolemia: a triglyceride (TG) of at least 150 mg/dL or a HDL-C of less than 40 mg/dL. The EPA-E group was orally administered with Epadel (Mochida Pharmaceutical Co., Ltd.) typically at an adult dose of 600 mg per administration and 3 times a day after the meal. However, in the case of abnormal serum TG, the dose could be increased to 900 mg per administration and 3 times a day. In both groups, pravastatin sodium (Mevalotin™ tablets and fine granules, Daiichi Sankyo Co., Ltd.), simvastatin (Lipovas™ tablets, Banyu Pharmaceutical Co., Ltd.), or atorvastatin calcium hydrate (Lipitor™ tablets, Astellas Pharma Inc. and Pfizer Inc.) was used for the base drug, and these drugs were orally administered according to the prescribed dosage regimen. More specifically, pravastatin sodium was orally administered at a daily dose of 10 to 20 mg in a single dose or two divided doses; simvastatin was orally administered at a daily dose of 5 to 20 mg in a single dose; atorvastatin calcium hydrate was orally administered at a daily dose of 10 to 40 mg in a single dose.

Results

The number of occurrence of cardiovascular events in the observation period of 5 years, incidence (%), and rate of suppression of the incidence of the cardiovascular events in the EPA-E group with respect to the control group are shown in Table 1 for each number of risk factors. The rate of suppression of the incidence of the cardiovascular events was calculated by the formula: [{(incidence in the control group)–(incidence in the EPA-E group)}/incidence in the control group]×100.

[Table 1]

TABLE 1

| Number of risk factors | Incidence in the control group (cases of occurrence/ all cases, %) | Incidence in the EPA-E group (cases of occurrence/ all cases, %) | Rate of suppression (%) |
|---|---|---|---|
| 0 | 14/1309 (1.1) | 11/1326 (0.8) | 22 |
| 1 | 29/2424 (1.2) | 25/2468 (1.0) | 15 |
| 2 | 46/2324 (2.0) | 34/2238 (1.5) | 23 |
| 3 | 29/1205 (2.4) | 28/1229 (2.3) | 5 |
| 4 | 9/216 (4.2) | 6/242 (2.5) | 40 |
| 1-2 | 75/4748 (1.6) | 59/4706 (1.3) | 21 |
| 1-3 | 104/5953 (1.7) | 87/5935 (1.5) | 18 |
| 1-4 | 113/6169 (1.8) | 93/6177 (1.5) | 18 |
| 2-3 | 75/3529 (2.1) | 62/3467 (1.8) | 16 |
| 2-4 | 84/3745 (2.2) | 68/3709 (1.8) | 18 |
| 3-4 | 38/1421 (2.7) | 34/1471 (2.3) | 14 |

The incidence (%) of cardiovascular events was found to increase with the increase in the number of risk factors. While the incidence was 1.1% for the risk factor number of 0 and 4.2% for the risk factor number 4 in the control group, the incidence was 0.8% in the risk factor number 0 and 2.5% for the case of risk factor number 4 in the group administered with the EPA-E. As evident from Table 1, for all cases of both groups with 1 to 4 risk factors, the cardiovascular event incidence was lower in the group administered with the EPA-E compared to the control group, and the cardiovascular events were suppressed by 5 to 40%. The effect of preventing occurrence of the cardiovascular events by the administration of the EPA-E was thereby confirmed for the hypercholesterolemia patients having the risk factors.

From the results of the trial as described above, the number of occurrence of cardiovascular events in the observation period of 5 years, incidence (%), and rate of suppression of the incidence of the cardiovascular events in the EPA-E group with respect to the control group were calculated for the male patients having at least two risk factors. The results are shown in Table 2. (The calculation was conducted by the same procedure as described above.)

[Table 2]

TABLE 2

| Number of risk factors | Incidence in the control group (cases of occurrence/ all cases, %) | Incidence in the EPA-E group (cases of occurrence/ all cases, %) | Rate of suppression (%) |
|---|---|---|---|
| 2-4 | 43/1053 (4.1) | 19/1065 (1.8) | 56 |

FIG. 1 is a graph prepared by plotting the incidence of the cardiovascular events in Y-axis and time after the start of the trial in X-axis.

As evident from Table 2 and FIG. 1, in the case of male patients having two or more risk factors, EPA-E significantly suppressed the occurrence of cardiovascular events. It was also confirmed that decrease in the incidence of the cardiovascular events was significant after 2 years or more from the start of the administration. At the end of the trial, the rate of suppression of the cardiovascular event occurrence was 56% compared to the control group (the value after correcting the dispersion between groups was 55%; see FIG. 1).

From the results of the trial as described above, the number of occurrence of cardiovascular events in the observation period of 5 years, incidence (%), and rate of suppression of the incidence of the cardiovascular events in the EPA-E group with respect to the control group were calculated for the patients exhibiting a triglyceride (TG) of at least 150 mg/dL and a HDL-C of less than 40 mg/dL as the risk factors. The results are shown in Table 3. (The calculation was conducted by the same procedure as described above.)

[Table 3]

TABLE 3

| Risk factor | Incidence in the control group (cases of occurrence/ all cases, %) | Incidence in the EPA-E group (cases of occurrence/ all cases, %) | Rate of suppression (%) |
|---|---|---|---|
| TG of at least 150 mg/dL and HDL-C of less than 40 mg/dL | 21/475 (4.4) | 11/482 (2.3) | 48 |

Figure 2:
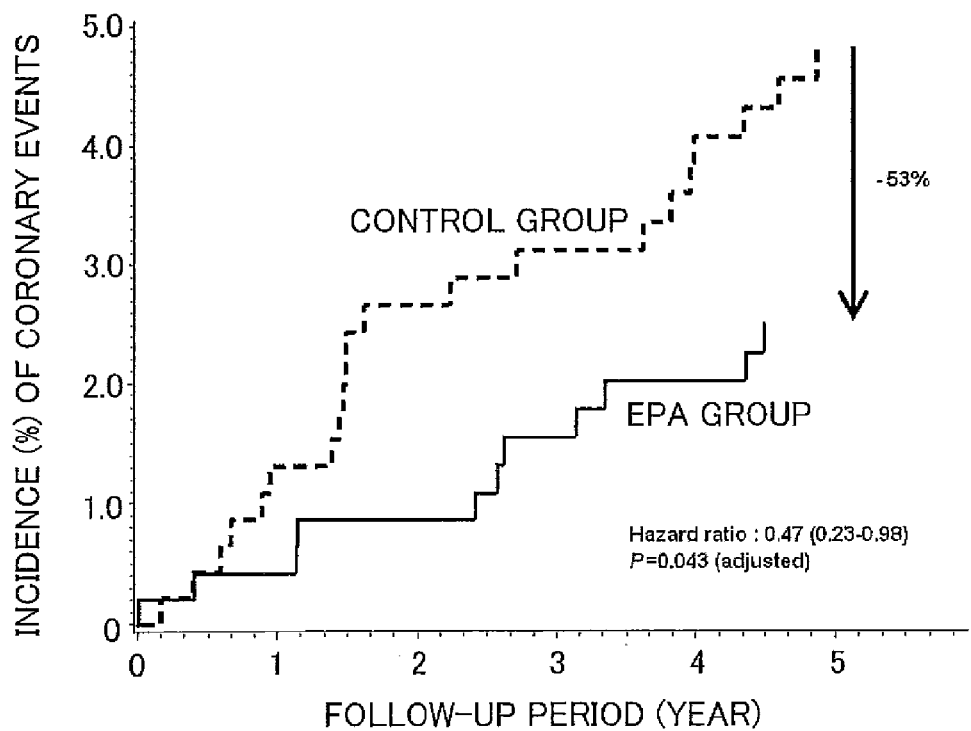
FIG. 2 is a graph prepared by plotting the incidence of the cardiovascular event in Y-axis and the time after the start of the trial in X-axis for patients having the risk factors of a triglyceride (TG) of at least 150 mg/dL and a HDL-C of less than 40 mg/dL.

FIG. 2 is a graph prepared by plotting the incidence of the cardiovascular events in Y-axis and time after the start of the trial in X-axis.

As evident from Table 3 and FIG. 2, EPA-E significantly suppressed occurrence of cardiovascular events in the patients having the risk factors of the triglyceride (TG) of at least 150 mg/dL and the HDL-C of less than 40 mg/dL. It was also confirmed that decrease in the incidence of the cardiovascular events was significant after 2 years or more from the start of the administration. At the end of the trial, the rate of suppression of the cardiovascular event occurrence was 48% compared to the control group (the value after correcting the dispersion between groups was 53%; see FIG. 2). This suggests that the composition containing EPA-E as its effective component effectively prevents the occurrence of the cardiovascular event in the patient having the serum TG/HDL-C ratio of at least 3.75. It is also to be noted that, while the events that occurred in the control group were fatal myocardial infarction, nonfatal myocardial infarction, new occurrence of angina and cardiovascular angioplasty, the events that occurred in the EPA-E group were either nonfatal myocardial infarction or new occurrence of angina, and occurrence of fatal events was not found in the EPA-E group.

In addition, in the group of patients having the risk factor of the triglyceride of at least 150 mg/dL, the occurrence of the cardiovascular events was suppressed by 15% in the EPA-E group compared to the control group; and in the group of patients having the risk factor of HDL-C of less than 40 mg/dL, the occurrence of the cardiovascular events was suppressed by 35% compared to the control group (both values are uncorrected values).

As described above, a significant effect of the EPA-E administration was confirmed for the prevention of the occurrence of the cardiovascular events in the hypercholesterolemia patients having the risk factors.

The invention claimed is:

1. A method of reducing occurrence of a cardiovascular event in a hypercholesterolemia patient consisting of:
    identifying a patient having triglycerides (TG) of at least 150 mg/DL and HDL-C of less than 40 mg/dL in a blood sample taken from the patient as the only risk factor of a cardiovascular event, wherein the patient has not previously had a cardiovascular event, and administering ethyl icosapentate in combination with a 3-hydroxy-3-methylglutaryl coenzyme A reductase inhibitor,
    wherein said 3-hydroxyl-3-methylglutaryl coenzyme A reductase inhibitor is administered to the patient at least one of before, during and after administering the ethyl icosapentate;
    wherein the content of the ethyl icosapentate is at least 96.5% by weight in relation to the total content of fatty acid that is simultaneously administered with the ethyl icosapentate; and
    wherein the 3-hydroxy-3-methylglutaryl coenzyme A reductase inhibitor is selected from the group consisting of pravastatin, lovastatin, simvastatin, fluvastatin, atorvastatin, pitavastatin, rosuvastatin, and salts thereof.

2. The method according to claim 1, wherein the ethyl icosapentate is orally administered at a dose of 1.8 g/day to 2.7 g/day.

3. The method according to claim 1, wherein the hypercholesterolemia patient is a male patient.

4. The method according to claim 1, wherein the ethyl icosapentate is administered daily for two years or more.

5. The method according to claim 1, wherein the cardiovascular event is a fatal cardiovascular event.

6. The method according to claim 1, wherein the hypercholesterolemia patient has a serum [triglyceride (TG)/HDL-C] ratio of at least 3.75.

7. The method according to claim 1, wherein the ethyl icosapentate is orally administered at a dose of 0.3 g/day to 6 g/day.

8. A method of reducing occurrence of a cardiovascular event in a hypercholesterolemia patient consisting of:
    identifying a patient having (i) total cholesterol (TC) of at least 220 mg/dL or LDL-cholesterol (LDL-C) of at least 140 mg/dL, and (ii) triglycerides (TG) of at least 150 mg/dL and HDL-C of less than 40 mg/dL in a blood sample taken from the patient as the only risk factors of a cardiovascular event, wherein the patient has not previously had a cardiovascular event, and
    administering ethyl icosapentate in combination with a 3-hydroxy-3-methylglutaryl coenzyme A reductase inhibitor,
    wherein said 3-hydroxyl-3-methylglutaryl coenzyme A reductase inhibitor is administered to the patient at least one of before, during and after administering the ethyl icosapentate;
    wherein the content of the ethyl icosapentate is at least 96.5% by weight in relation to the total content of fatty acid that is simultaneously administered with the ethyl icosapentate; and
    wherein the 3-hydroxy-3-methylglutaryl coenzyme A reductase inhibitor is selected from the group consisting of pravastatin, lovastatin, simvastatin, fluvastatin, atorvastatin, pitavastatin, rosuvastatin, and salts thereof.

9. The method according to claim 8, wherein the ethyl icosapentate is orally administered at a dose of 1.8 g/day to 2.7 g/day.

10. The method according to claim 8, wherein the hypercholesterolemia patient is a male patient.

11. The method according to claim 8, wherein the ethyl icosapentate is administered daily for two years or more.

12. The method according to claim 8, wherein the cardiovascular event is a fatal cardiovascular event.

13. The method according to claim 8, wherein the hypercholesterolemia patient has a serum [triglyceride (TG)/HDL-C] ratio of at least 3.75.

14. The method according to claim 8, wherein the ethyl icosapentate is orally administered at a dose of 0.3 g/day to 6 g/day.

* * * * *